United States Patent
Jeanneret

(10) Patent No.: US 7,276,636 B2
(45) Date of Patent: Oct. 2, 2007

(54) STYRENE PROCESS WITH RECYCLE FROM DEHYDROGENATION ZONE

(75) Inventor: John J. Jeanneret, Western Springs, IL (US)

(73) Assignee: UOP LLC, Des Plaines, IL (US)

( * ) Notice: Subject to any disclaimer, the term of this patent is extended or adjusted under 35 U.S.C. 154(b) by 182 days.

(21) Appl. No.: 11/205,657

(22) Filed: Aug. 17, 2005

(65) Prior Publication Data
US 2005/0288539 A1 Dec. 29, 2005

Related U.S. Application Data

(63) Continuation of application No. 10/252,987, filed on Sep. 23, 2002, now Pat. No. 7,094,939.

(51) Int. Cl.
*C07C 2/66* (2006.01)
*C07C 2/64* (2006.01)

(52) U.S. Cl. ............... 585/323; 585/319; 585/440; 585/470; 585/446

(58) Field of Classification Search ........... 585/323, 585/319, 440, 470, 446
See application file for complete search history.

(56) References Cited

U.S. PATENT DOCUMENTS

| | | | |
|---|---|---|---|
| 3,409,689 A | 11/1968 | Ward | 260/669 |
| 3,525,776 A | 8/1970 | Berger | 260/669 |
| 4,252,615 A | 2/1981 | Watson | 203/9 |
| 4,417,085 A | 11/1983 | Watson et al. | 585/440 |
| 4,469,558 A | 9/1984 | Watson | 202/154 |
| 4,492,675 A | 1/1985 | Watson et al. | 422/187 |
| 4,628,136 A | 12/1986 | Sardina | 585/441 |
| 5,043,500 A | 8/1991 | Tagamolila | 585/319 |
| 5,869,717 A | 2/1999 | Frame et al. | 585/5 |
| 6,395,943 B1 | 5/2002 | Kurek et al. | 585/5 |

OTHER PUBLICATIONS

James, Denis H., et al. Styrene *Ullmann's Encyclopedia of Industrial Chemistry*, 5th Ed., vol. A25, VCH Publishers, New York, USA, 1994 VCH Verlagsgesellschaft 3-527-20125-4/94 pp. 329-344.
Li, C.H., et al. Styrene *Encyclopedia of Chemical Processing and Design*, vol. 55, Marcel Dekker, Inc., New York, USA, 1996 ISBN: 0-8247-2606-5 pp. 197-217.
Winkler, R.E., et al. Inhibition of the Thermal Polymerization of Styrene by N-Phenyl-N'-Isopropyl-p-Phenylenediamine *Journal of Polymer Science: Part A: Polymer Chemistry*, vol. 26, John Wiley & Sons, Inc. 1988 pp. 2853-2958.
Lummus/UOP Classic SM™ Process: UOP, Des Plaines, IL 1997 *UOP 2699C-2 597AD4B*.
Ethylbenzene/"Classic" Styrene Monomer ABB Lummus Global, 1515 Broad Street, Bloomfield, NJ, 07003-3096 USA, Mar. 29, 2001.

*Primary Examiner*—Thuan Dinh Dang
(74) *Attorney, Agent, or Firm*—James C Paschall; David J Piasecki

(57) ABSTRACT

A styrene process is disclosed that uses a dehydrogenation reactor and a transalkylation reactor and in which a significant portion of the benzene, the inhibitors, or both, recovered from the dehydrogenation reactor passes to the transalkylation reactor. The process disclosed herein can also use an alkylation reactor and can increase the run length of the alkylation catalyst.

17 Claims, 1 Drawing Sheet

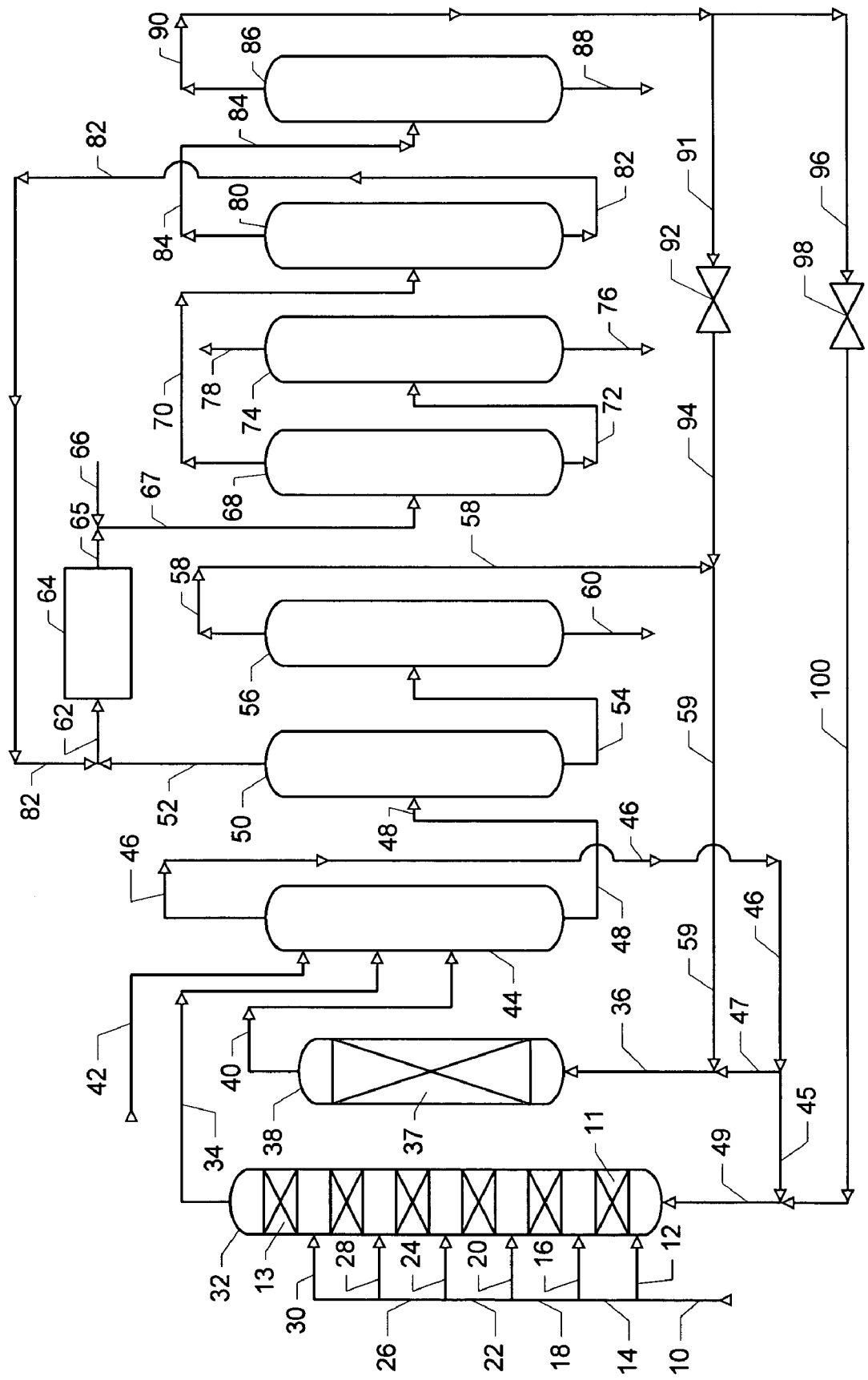

STYRENE PROCESS WITH RECYCLE FROM DEHYDROGENATION ZONE

CROSS-REFERENCE TO RELATED APPLICATION

This application is a Continuation of U.S. application Ser. No. 10/252,987, filed on Sep. 23, 2002, now U.S. Pat. No. 7,094,939 which is incorporated herein by reference in its entirety.

FIELD OF THE INVENTION

This invention relates generally to a process for the production of styrene by the dehydrogenation of ethylbenzene.

BACKGROUND OF THE INVENTION

Styrene (phenylethylene, vinylbenzene) is commonly produced in a two-step process. First, ethylbenzene (EB) is formed by alkylating benzene, by transalkylating polyethylbenzenes (PEBs), or by both. Then, the EB is dehydrogenated to produce styrene. Styrene is an important monomer used in the manufacture of many plastics.

In the first step, benzene is alkylated with an ethylating agent such as ethylene to form EB. Diethylbenzenes (DEBs), triethylbenzenes (TEBs), and other heavier PEBs are also formed. To maximize EB formation, the PEBs are usually transalkylated with benzene to form more EB. When both alkylation and transalkylation are used, two separate reactors, each with its own catalyst, are often employed. Both the alkylation and transalkylation effluents flow to a distillation train, which recovers benzene, EB, and the light PEBs (DEBs and TEBs) as distillates in three distillation columns in series. These columns are called the benzene column, the EB column, and the PEB column. Benzene distillate from the benzene column is recycled to the alkylation and transalkylation reactors, and the light PEBs distillate is recycled to the transalkylation reactor. Examples of distillation trains for separating EB produced by alkylation and transalkylation are described in U.S. Pat. Nos. 4,169,111 and 4,891,458; PCT Publication WO 96/20148; and Catalysis of Organic Reactions, edited by W. R. Moser, Marcel Dekker, Inc., New York, USA, 1981, at pages 39-50.

In the second step, the EB is dehydrogenated to styrene in the presence of steam, which supplies the sensible heat needed for the endothermic reaction. Byproducts of this dehydrogenation reaction include benzene, toluene, and heavies (tar). The separation of the dehydrogenation effluent (which the prior art sometimes refers to as "crude styrene") to recover styrene from steam, unreacted EB, and the byproducts is reasonably straightforward using three or four distillation columns.

In one distillation scheme, a first column separates or splits the effluent into EB and lighter components in its overhead and styrene and heavier components in its bottoms. A second column separates the first column's overhead into benzene and toluene in its overhead and EB in its bottoms for recycling EB to the dehydrogenation reactor. A third column separates the first column's bottoms into styrene product in its overhead and heavies (tar) in its bottom. U.S. Pat. No. 3,409,689, the teachings of which are hereby incorporated herein by reference, describes this scheme. According to this patent, the hydrocarbonaceous phase removed from the phase separation section passes into an effluent splitter distillation column. This first column separates or splits the effluent into EB and lighter components in an overhead stream and into styrene and heavier components in its bottoms stream. This overhead stream passes to a second distillation column called an EB recovery column to produce an overhead stream containing benzene and toluene and a bottom product containing EB. The EB product is recycled. The bottom stream of the effluent splitter column flows to styrene distillation column to produce purified styrene as an overhead stream and a bottom stream containing heavies.

Another distillation flow scheme recovers benzene-toluene, EB, and styrene as distillates in three distillation columns in series, as described in U.S. Pat. No. 3,525,776, the teachings of which are hereby incorporated herein by reference. In this patent, the hydrocarbonaceous phase removed from the phase separation section passes into a benzene-toluene recovery distillation column. This first column operates at a subatmospheric pressure to allow its operation at lower temperatures and hence reduce the rate of styrene polymerization. Within the benzene-toluene recovery column a separation of benzene and toluene from the effluent occurs to produce an overhead stream which is substantially free of styrene and EB. This overhead stream preferably contains at least 95 mol-% benzene and toluene. The bottoms stream of the benzene-toluene recovery column passes into an EB recovery distillation column from which EB is removed as an overhead product and recycled. The bottoms stream of this EB recovery column then passes to a styrene column to produce purified styrene as an overhead stream and a bottom stream containing heavies.

Using either distillation flow scheme, a fourth column can further purify the styrene product. For further information and examples of these distillation trains, see U.S. Pat. No. 4,252,615 (Watson); Ullmann's Encyclopedia of Industrial Chemistry, 5th Edition, Vol. A25, VCH Publishers, New York, USA, 1994, at pages 329-344, and especially at pages 334-5; Encyclopedia of Chemical Processing and Design, Vol. 55, Marcel Dekker, Inc., New York, USA, 1996, at pages 197-217, and especially at pages 203-205; the technical sheet entitled "Lummus/UOP Classic SM Process," UOP LLC, Des Plaines, Ill., USA, 1997; and the technical sheet, "Ethylbenzene/'Classic' Styrene Monomer," ABB Lummus Global, Bloomfield, N.J., USA, Mar. 29, 2001.

Typically the only benzene present in the dehydrogenation zone is the relatively small amount that is formed as a byproduct of the reactions that take place during EB dehydrogenation. This benzene is subsequently recovered in the benzene-toluene fraction. The quantity of byproduct benzene is usually considered to be so commercially insignificant that operators of some styrene plants simply reject the entire benzene-toluene fraction from the plant for some other use or to disposal. However, operators of other styrene plants may either lack an alternative use for this fraction or may wish to avoid the disposal costs. Also, operators may introduce benzene to the dehydrogenation zone as described in U.S. Pat. Nos. 3,409,689 and 3,525,776, and so more benzene than just byproduct benzene may be present in the benzene-toluene fraction. These styrene plant operators distill the benzene (including byproduct benzene) from the benzene-toluene fraction and then recycle it to previously mentioned distillation train that is used for separating the alkylation and transalkylation effluents. In some cases, this benzene from the dehydrogenation zone is introduced into the first column (benzene column) of the distillation train, where it is recovered in the benzene-containing overhead stream. In other cases, it is combined directly with some or all the overhead stream of the benzene column.

Since benzene is, of course, a major feedstock for both the alkylation and transalkylation reactors, the benzene column of this distillation train or its overhead stream is also the destination for other, much larger flows of benzene. Because benzene is often supplied to these reactors in a large molar excess, the alkylation and transalkylation reactor effluents each carry a major flow of benzene to the benzene column. In addition, makeup benzene enters the benzene column or into that column's overhead. The effect of combining these various flows of benzene in the benzene column or its overhead is that the distillation train for the alkylation and transalkylation reactor effluents produces what amounts to a relatively homogeneous stream of benzene for recycling to the alkylation and transalkylation reactors. The relatively small amount of benzene arriving from the dehydrogenation zone is significantly diluted in this much larger stream.

That flow of recycle benzene, in turn, is split into two portions, with one portion passing to the alkylation reactor and the other to the transalkylation reactor. The split of benzene between the alkylation and transalkylation reactors depends on the operating conditions of the two zones, but generally less than 30% of the benzene recovered from the dehydrogenation zone passes to the transalkylation reactor. Except for the capital and operating costs of the additional distillation column needed to separate the benzene-toluene fraction, persons of ordinary skill in the art of styrene plants have viewed recycling the benzene from the dehydrogenation zone in this manner as technically-sound, as economically-acceptable, and as having no significant deleterious effect on the process.

While the distillation flow schemes for separating the alkylation, transalkylation, and dehydrogenation effluents are reasonably straightforward, it is well known that difficulties arise in distilling the dehydrogenation effluent. One difficulty is corrosion, since acidic aqueous solutions tend to condense in the cooler overhead sections of the distillation columns. Another difficulty is styrene polymerization in the hotter sections (typically from about 90° C. to about 150° C. (194° F. to 302° F.)) of the columns, since styrene tends to autopolymerize.

To prevent corrosion and polymerization, small amounts of inhibitors are added to the dehydrogenation effluent and/or the distillation train. The optimum choice of inhibitor(s) involves weighing many factors besides inhibition effectiveness, including cost, availability, volatility, toxicity, thermal stability, solubility, viscosity, whether oxygen is present, and the nature of the resultant residue. While individual styrene plants may use different inhibitors, most if not all styrene plants today use at least one inhibitor. The exact chemical compositions of inhibitors in commercial use today are not widely known, since the commercial suppliers of these inhibitors tend to keep this information secret. However, since the chemistry of both corrosion and polymerization is well understood, certain general characteristics of these inhibitors are well known to persons of ordinary skill in the art.

As concerns corrosion inhibitors, it is generally believed that many may be nitrogen compounds. These nitrogen compounds are believed to possibly include primary, secondary, and tertiary amines. One or more hydrogen atoms of the amine may be replaced with one or more alkyl groups or hydroxy alkyl groups. It is believed ethanolamine and diethanolamine may be in use. Other nitrogen compounds thought to possibly be in use include diamines and triamines. Each nitrogen atom of the diamines and triamines may be linked to one or more hydrogen atoms, alkyl groups, or hydroxy alkyl groups. The possible diamines may include ethylene diamine. Other possible classes of nitrogen compounds that may be in use include amides, N-(acyloxy)-alkane amines, dihydro-1-alkyl-N-substituted imidazoles (e.g., dihydro-1-alkyl-N-hydroxyalkane-imidazoles and dihydro-1-alkyl-N-aminoalkane-imidazoles), trialkylaminium dialkyl phosphates, and trialkylaminium alkyl hydrogen phosphates. Besides the corrosion inhibitors listed here, others may be in use.

As for polymerization inhibitors, the previously-mentioned reference in Ullmann's Encyclopedia of Industrial Chemistry states that at one time sulfur was used, but many new inhibitors are aromatic compounds that have amino, nitro, or hydroxy groups, including phenylenediamines, dinitrophenols, and dinitrocresols. It is believed that aromatic compounds that have nitroso groups are also in use as polymerization inhibitors. The "Background of the Invention" section of U.S. Pat. No. 6,395,943 B1 (Kurek and Frame) summarizes the extensive art disclosing a variety of compounds which are claimed to inhibit polymerization. These include N,N-nitroso-methylaniline; N-nitrosodiphenyl amine in combination with dinitro-o-cresol; N-nitroso aniline derivatives; a mixture of dinitro-p-cresol and N-nitroso-diphenyl amine; alkyl substituted p-nitroso phenol in combination with p-nitroso phenol; N-nitrosophenyl-hydroxylamine plus hydroquinone monomethyl ether; a phenylene-diamine compound plus a hydroxyalkylhydroxylamine compound; 1-oxy-2,2,6,6-tetramethylpiperidine plus an aromatic nitro compound; a phenylenediamine compound plus a hindered phenol compound; the reaction product of a C9-C20 alkyl phenol with sulfuric and nitric acid and optionally an aryl or alkyl-substituted phenylenediamine; 3,5-di-tert-butyl-4-hydroxy-N,N-dimethyl benzyl amine; 4-acetylamino-2,2,6,6-tetramethyl piperidine N-oxyl in combination with 4-nitroso phenol; phosphite compounds, nitrosoamine compounds or phenol compounds; the ammonium salt of N-nitrosophenyl hydroxylamine; nitrosophenols plus dicyclohexyl-ammonium nitrate; substituted nitrosobenzene; p-nitroso phenol plus p-t-butyl catechol; N-nitroso compound, e.g., N-nitroso-diphenylamine and a catechol, e.g., p-t-butylcatechol; and N-nitroso derivates of unsubstituted or dialkyl substituted phenylenediamine. U.S. Pat. No. 6,395,943 B1 itself discloses a mixture of at least one nitroso compound such as N,N'-di-2-butyl-N,N'-dinitroso-1,4-diaminobenzene and a dinitrophenol compound such as dinitrocresol, and optionally a stabilizer compound such as an N,N'-dialkyl substituted 1,4-diaminobenzene.

When corrosion inhibitors are used, they are typically added into the upper portions or overhead sections of the distillation columns. When polymerization inhibitors are used, they are typically added to distillation mixtures containing styrene or distillation columns processing styrene. Typically, any polymerization inhibitor is added to the dehydrogenation effluent stream passing to the first distillation column in the dehydrogenation separation section. When inhibitors are used, generally less than 30% of the inhibitors recovered from the dehydrogenation zone passes to the transalkylation reactor. For further information on the use of specific polymerization inhibitors in styrene production, see Journal of Polymer Science: Part A: Polymer Chemistry, Vol. 26, 2853-2858 (1988); U.S. Pat. No. 5,869,717 (Frame et al.) and the previously mentioned references of U.S. Pat. No. 4,252,615, Ullmann's Encyclopedia of Industrial Chemistry, Encyclopedia of Chemical Processing and Design, the UOP LLC technical sheet, and the ABB Lummus Global technical sheet.

In order to be commercially profitable, industrial styrene plants must operate uninterrupted and for extended periods of time. Shutdowns must be minimized. One obstacle to maintaining continuous production is that the alkylation catalyst deactivates over time. It is known, of course, that the rate of catalyst deactivation can be decreased somewhat by operating at a high benzene/olefin molar ratio in alkylation, and that deactivated catalyst can be reactivated to some extent by contacting the catalyst with benzene in a regeneration step. However, it is also known that some catalyst deactivation occurs that can be neither slowed by operation at higher benzene/olefin molar nor reversed by regenerating the catalyst with benzene. Catalyst deactivation that cannot be reversed by typical regeneration procedures is sometimes referred to as "permanent," either because it sometimes requires additional reactivation measures beyond contacting the catalyst with benzene or because it sometimes requires shutting down and replacing the catalyst.

Methods are sought to minimize deactivation of the alkylation catalyst.

SUMMARY OF THE INVENTION

In the styrene process disclosed herein, a significant portion of the benzene, the inhibitors, or both, in a recycle stream recovered from the dehydrogenation zone passes to the transalkylation zone rather than to an alkylation zone.

It has now been recognized that the inhibitors used in the dehydrogenation zone not only are present in this recycle stream but also can rapidly deactivate the alkylation catalyst when they pass to the alkylation zone in significant quantities, as they do in the prior art processes. Even when the inhibitors are diluted before entering the alkylation zone with copious flows of benzene from elsewhere in the process, the inhibitors nevertheless can have a significant deleterious effect on the alkylation catalyst. Therefore, compared to the prior art processes, the disclosed process passes less benzene and/or inhibitors from this recycle stream to the alkylation zone.

One of the important advantages of the disclosed process is that it can improve efficiency and profitability of the styrene plant by helping to extend the run length of the alkylation catalyst. Run length is the period of time during which a catalyst has enough activity to promote reactions efficiently and economically. The longer the run length, the less frequent is the need for catalyst regeneration or replacement, and the more profitable is the operation of the styrene plant. Because the disclosed process passes less benzene and/or inhibitors from the recycle stream to the alkylation reactor, the effect of this stream on the alkylation catalyst can be less. This, in turn, can extend the run length of the alkylation catalyst.

While the process disclosed herein does pass more benzene and/or inhibitors from the recycle stream to the transalkylation reactor than do the prior art processes, this can be an advantage because it has now been recognized that the any adverse effect of this recycle stream can be less on the transalkylation catalyst than on the alkylation catalyst. Passing more of the recycle stream to the transalkylation catalyst does not necessarily shorten the run length of the transalkylation catalyst. Without being bound to any particular theory, it is believed that this is because of differences in the compositions and amounts of the alkylation and transalkylation catalysts used in the styrene plant. However, even if passing more of the recycle stream did lengthen the alkylation catalyst run length at the expense of shortening the transalkylation catalyst run length, the process disclosed herein would nevertheless be more economical than the prior art processes. This is because transalkylation catalyst typically costs less than alkylation catalyst and would be cheaper to replace than alkylation catalyst.

In one embodiment, the process disclosed herein is for producing styrene. Benzene and a PEB react in a transalkylation reactor to form EB, which is dehydrogenated in a dehydrogenation reactor to form styrene. Styrene and benzene are recovered from the dehydrogenation reactor. At least 33 percent of the benzene recovered from the dehydrogenation reactor passes to the transalkylation reactor. In other embodiments, at least 50 percent, at least 75 percent, or all of the benzene recovered from the dehydrogenation passes to the transalkylation reactor.

In another embodiment, the process disclosed herein is a styrene process. Benzene and a PEB react in a transalkylation reactor to form EB. The EB is dehydrogenated in a dehydrogenation reactor to form styrene. A dehydrogenation reactor effluent comprising styrene is withdrawn from the dehydrogenation reactor effluent. At least a portion of the dehydrogenation reactor effluent passes to a dehydrogenation separation section, from which styrene is recovered. A first inhibitor element component is introduced to the dehydrogenation separation section. A recycle stream comprising a second inhibitor element component is recovered from the dehydrogenation separation section. At least 33% of the second inhibitor element component recovered from the dehydrogenation separation section in the recycle stream passes to the transalkylation reactor. In other embodiments, at least 50 percent, at least 75 percent, or all of the second inhibitor element component recovered from the dehydrogenation separation section in the recycle stream passes to the transalkylation reactor. In other embodiments, the first inhibitor element component is the same as the second inhibitor element component, or the first or second inhibitor element components are sulfur or nitrogen.

In another embodiment, this invention is a styrene process in which the portion of the benzene, the inhibitors in the benzene, or both, that passes to the transalkylation reactor is greater than that which passes to an alkylation reactor.

INFORMATION DISCLOSURE

U.S. Pat. No. 3,409,689 describes a dehydrogenation process in which toluene is recovered from a distillation train and is recycled to the dehydrogenation reactor.

U.S. Pat. No. 3,525,776 describes a styrene process in which a benzene-containing stream from the benzene column in the styrene distillation train is recycled to the alkylation and transalkylation reactors.

U.S. Pat. No. 4,252,615 describes using a polymerization inhibitor in a process for producing vinyl aromatic compounds.

U.S. Pat. No. 4,417,085 and 4,492,675 describe product recovery techniques directed to the recovery of vinyltoluene via fractionation and the use of chemical additives to inhibit polymerization.

U.S. Pat. No. 4,469,558 describes the use of inhibitors and alternative fractionation techniques for readily polymerizable vinyl aromatic compounds.

U.S. Pat. No. 5,043,500 describes introducing an inhibitor into the distillation train of a dehydrogenation zone. The teachings of U.S. Pat. No. 5,043,500 are hereby incorporated herein by reference.

U.S. Pat. No. 5,869,717 describes a process for inhibiting the polymerization of vinyl aromatics. The teachings of U.S. Pat. No. 5,869,717 are hereby incorporated herein by reference.

U.S. Pat. No. 6,395,943 B1 describes a process for inhibiting the polymerization of styrene during its distillation.

Ullmann's Encyclopedia of Industrial Chemistry, 5th Edition, Vol. A25, VCH Publishers, New York, USA, 1994, at pages 329-344, describes a styrene plant into which inhibitors are introduced.

Encyclopedia of Chemical Processing and Design, Vol. 55, Marcel Dekker, Inc., New York, USA, 1996, at pages 197-217, describes a styrene plant into which in inhibitors are introduced.

The technical sheet entitled "Lummus/UOP Classic SM Process," UOP LLC, Des Plaines, Ill., USA, 1997 shows and describes a process flow scheme of a styrene plant into which polymerization inhibitors are added.

The technical sheet, "Ethylbenzene/'Classic' Styrene Monomer," ABB Lummus Global, Bloomfield, N.J., USA, Mar. 29, 2001 shows a process flow diagram of a styrene plant into which polymerization inhibitors are added.

BRIEF DESCRIPTION OF THE DRAWING

The drawing is a process flow diagram illustrating an embodiment of the invention.

DETAILED DESCRIPTION OF THE INVENTION

The process disclosed herein will first be described in terms of an embodiment having an alkylation zone, a transalkylation zone, and a dehydrogenation zone, because it is believed that this will be the most commonly used embodiment of the process. However, this description, and especially the description of this most common embodiment, is not intended to limit the scope of this invention as set forth in the claims. The source of the PEBs charged to the transalkylation zone is not critical to the process disclosed herein, and sources other than an alkylation zone are possible. The PEB source can be an external supply. However, since an alkylation zone is the most common source, the embodiment having an alkylation zone is described first.

The alkylation zone may be any suitable alkylation zone that makes PEBs. As a practical matter, nearly every alkylation zone for EB production from benzene and ethylene make PEBs too. Since the desired product of the process is styrene, in one embodiment the alkylation zone has a high selectivity to EB.

The alkylation zone usually includes an alkylation reactor and an associated separation section for separating the EB product from alkylation byproducts and unreacted reactants. The description of the alkylation zone that follows is not intended limit the broad scope of the claims.

Since alkylation zones for EB production from benzene and ethylene usually make PEBs too. In a conventional alkylation zone, an aromatic feed stream flows to an alkylation reactor and an olefinic feed stream is introduced stagewise to the alkylation reactor. The alkylation reactor can comprise one or more alkylation catalyst beds, and two-bed reactors are common. The number of catalyst beds in a reactor is usually less than six. More than one alkylation reactor may be used. The number of reactors is generally less than eight. Vessels suitable as reactors are known to persons of ordinary skill in the art of hydrocarbon processing.

The alkylation reaction conditions are not critical to the process disclosed herein, since PEBs are formed even when the alkylation reaction conditions are chosen to maximize EB production. Persons of ordinary skill in the art can choose the alkylation reaction conditions from very broad ranges to achieve desired yields or alkylation catalyst run lengths. One of the most important operating variables for alkylation is the molar ratio of phenyl groups per ethyl group, which is often referred to as the phenyl/ethyl ratio. The numerator of this ratio is the number of moles of phenyl groups passing through the reactor during a specified period of time. The number of moles of phenyl groups is the sum of all phenyl groups, regardless of the compound in which the phenyl group happens to be. For example, one mole of benzene, one mole of EB, one mole of DEB, and one mole of triethylbenzene (TEB) each contribute one mole of phenyl group to the sum of phenyl groups. The denominator of this ratio is the number of moles of ethyl groups passing through the reactor during the same specified period of time. The number of moles of ethyl groups is the sum of all ethyl and ethenyl groups, regardless of the compound in which the ethyl or ethenyl group happens to be, except that paraffins are not included. For example, one mole of EB contributes one mole of ethyl group to the sum of ethyl groups, whereas one mole of DEB contributes two moles of ethyl groups and one mole of TEB contributes three moles of ethyl groups. Paraffins, such as ethane, propane, n-butane, isobutane, and higher paraffins, are excluded from the computation of the number of moles of ethyl groups. The phenyl/ethyl ratio can be from about 25:1 to about 0.75:1, or in other embodiments less than 1:1 or even less than 0.75:1. A phenyl/ethyl ratio of below 6:1 is common.

The alkylation reaction temperature may be from about 100 to about 290° C. (212 to 554° F.). The alkylation reactor inlet temperature may be from about 180 to about 260° C. (356 to 500° C.) in one embodiment, and from about 190 to about 220° C. (374 to 428° C.) in another embodiment. Depending on the mass flows in the reactor, the temperature rise across the reactor may be from about 5 to about 190° C. (9 to 342° F.) in one embodiment, about 5 to about 50° C. (9 to 90° F.) in another embodiment, and about 5 to about 25° C. (9 to 45° F.) in yet another embodiment. The alkylation pressure is generally high enough to ensure at least a partial liquid phase. The weight hourly space velocity (WHSV) of ethylene can be from about 0.01 to about 2.0 hr−1, and the WHSV of benzene can be from about 0.3 to about 480 hr−1. As used herein, the abbreviation "WHSV" means weight hourly space velocity, which is defined as the weight flow rate per hour divided by the catalyst weight, where the weight flow rate per hour and the catalyst weight are in the same weight units. Some of the alkylation reactor effluent may be recycled, with or without cooling, to the alkylation reactor to act as a heat sink to control the temperature in the alkylation catalyst bed(s).

The alkylation catalyst can be any suitable catalyst, including any of the hereinafter-described transalkylation catalysts. In particular, the alkylation catalyst may comprise zeolite beta, and more particularly the surface-modified zeolite beta disclosed in U.S. Pat. No. 5,723,710, combined with an alumina or silica binder.

The principal reactions that occur in the alkylation reactor are the alkylation of the benzene by ethylene to produce EB and PEBs, which can include DEBs, TEBs, and higher PEBs. The alkylation reactor effluent stream is thus a mixture of EB and PEBs. In addition, the reactor effluent stream usually contains unreacted benzene and may also contain light ends such as C1 to C3 paraffins. But any ethylene in the alkylation reactor effluent stream is usually small.

The alkylation reactor effluent usually passes to a separation section. This separation section may be dedicated to separating only the alkylation reactor effluent, or it may be used to separate both the alkylation and transalkylation reactor effluents. In either case, a number of separation stages are typically needed to separate the EB from the PEBs byproducts and benzene. A number of combinations of columns and separators can be used to recover the EB product and to produce recycle streams of benzene and PEBs for transalkylation. Typically, a first column (benzene column) separates benzene from the remaining heavier components of the transalkylation effluent stream. One or more additional separation columns (EB column) separate the EB from byproduct streams that contain heavier byproducts, such as DEB and TEB. Heavies byproducts that are not suitable or are not desirable for transalkylation are usually rejected from the process.

In the arrangement of columns previously described, the alkylation effluent generally passes to the first column, either separately or combined in a single stream with the transalkylation effluent stream. Alternatively, some or all of the alkylation effluent can pass to the transalkylation reactor, with the remainder if any flowing to the separation stages.

Turning now to the transalkylation zone, transalkylation produces EB by transalkylating benzene and PEBs. The PEBs may include DEBs, TEBs, and higher PEBs. Transalkylating is a type of disproportionation reaction. Examples of conversions that take place in transalkylation are converting PEB to EB, and benzene to EB. Another conversion that may take place is a higher PEB converting to a lower PEB.

The transalkylation zone may be any suitable zone. The transalkylation zone usually includes a transalkylation reactor and an associated separation section for separating the EB product from transalkylation byproducts and unreacted reactants. As mentioned previously, the separation section for the transalkylation effluent may be used in common to separate both the alkylation and transalkylation reactor effluents, or it may be dedicated to separating only the transalkylation reactor effluent.

The description that follows of the transalkylation zone is not intended to limit the broad scope of the claims. The transalkylation zone can be of many different variations. The transalkylation reactor generally contains a catalyst that promotes the transalkylation reactions. The transalkylation catalyst for the process disclosed herein may be one of a class of aluminosilicate molecular sieves known as zeolites. The zeolitic molecular sieves suitable for use in the present invention are crystalline aluminosilicates which in the calcined form may be represented by the general formula:

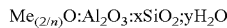

$$Me_{(2/n)}O:Al_2O_3:xSiO_2:yH_2O$$

where Me is a cation, n is the valence of the cation, x is a value of from about 5 to about 100, and y has a value of from about 2 to 10. Detailed descriptions of zeolites may be found in D. W. Breck, Zeolite Molecular Sieves, John Wiley and Sons, New York, 1974, and in other standard references. Suitable zeolites for the transalkylation catalyst include zeolite Y, zeolite beta, ZSM-5, PSH-3, MCM-22, MCM-36, MCM-49, and MCM-56. In one embodiment, the transalkylation catalyst comprises a zeolite Y that is essentially free of residual non-H⁺ cations, by which it is meant that the non-H⁺ cation content of the zeolite Y is less than 200 wppm calculated as $NH_3$ equivalents.

The zeolite is generally present in an amount of at least 50 wt-% of the catalyst and more preferably in an amount of at least 90 wt-% of the transalkylation catalyst. In most cases, the balance of the transalkylation catalyst other than the zeolite is a refractory inorganic oxide binder. In one embodiment the inorganic oxide is alumina, such as gamma-alumina, eta-alumina, and mixtures thereof. Where the catalyst comprises a zeolite and an inorganic oxide, the zeolite content may be from 5 to 99 wt-% of the catalyst, and the inorganic oxide may be from 1 to 95 wt-% of the catalyst. In one embodiment the transalkylation catalyst is zeolite Y with an alumina or silica binder.

Other zeolites for the transalkylation catalyst are the zeolite beta as disclosed in U.S. Pat. Nos. 4,891,458 and 5,081,323, and the surface-modified zeolite beta which is disclosed in U.S. Pat. No. 5,723,710. The teachings of U.S. Pat. Nos. 4,891,458; 5,081,323; and 5,723,710 are incorporated herein by reference.

The transalkylation reaction can be carried out in a broad range of operating conditions that result in a high conversion of diethylbenzene (DEB) to EB. DEB conversion is limited by equilibrium governed mainly by the ratio of phenyl groups per ethyl group and is generally greater than 30% and in one embodiment about 50%. Operating conditions generally include a temperature of from about 99° C. (210° F.) to about 290° C. (554° F.). The transalkylation pressure would generally be set so that the reactants are at least partially in the liquid phase, such as from about 101 to about 13169 kPa(g) (15 to 1910 psi(g)) or from about 1013 to about 5065 kPa(g) (147 to 735 psi(g)). The liquid hourly space velocity (LHSV) may be any value suitable for the transalkylation reactions, such as from 0.5 to 50 hr−1, or in other embodiments from 0.5 to 5.0 hr−1 or from 2.0 to 2.3 hr−1. As used herein, the abbreviation "LHSV" means liquid hourly space velocity, which is defined as the volumetric flow rate of liquid per hour divided by the catalyst volume, where the liquid volume and the catalyst volume are in the same volumetric units. In case the inhibitor has a deleterious effect on the transalkylation catalyst, a larger amount of transalkylation catalyst can be used in order to lengthen the run length of the transalkylation catalyst. The water concentration is typically less than 200 wppm, and preferably less than 20 wppm, and more preferably less than 5 wppm.

The phenyl/ethyl ratio is a key operating variable for transalkylation because the equilibrium conversion of PEBs is a function of the phenyl/ethyl ratio. The phenyl/ethyl ratio can be any suitable ratio to achieve the desired extent of transalkylation reactions, such as from 10:1 to 1:1 in one embodiment or from 7:1 to 2:1 in another embodiment. Where the transalkylation feed consists of only benzene and DEB, the phenyl/ethyl ratio may be computed from the molar ratio of benzene per DEB, which is referred to as the benzene/DEB ratio, by using the mathematical formula, phenyl/ethyl ratio=1/2×(benzene/DEB ratio+1). This mathematical formula is sufficiently accurate as an approximation of the phenyl/ethyl ratio when the EB content or the TEB content of the transalkylation feed is less than 1.0 vol-%.

The transalkylation reactor may be operated and arranged in any manner that provides the desired operating conditions and the required contacting of reactants and catalyst. A single contacting stage in transalkylation is routinely used, in part because the transalkylation reactions are neither very exothermic nor very endothermic.

The transalkylation effluent stream contains not only the desired EB but also unreacted transalkylation reactants as well as transalkylation byproducts. Of the transalkylation reactants, benzene is usually the most abundant, because in transalkylation benzene is generally present in a stoichiometric excess to the PEBs. DEBs in the transalkylation feed also are generally present in the transalkylation effluent stream because the DEB conversion in transalkylation is limited by equilibrium to less than 100%. Higher PEBs such as TEBs and tetra-EBs also may be present in the transalkylation effluent, either as an unreacted transalkylation reactant or as a transalkylation byproduct from the reaction of a PEB with another PEB rather than with benzene.

A number of separation stages are needed to separate the EB from the byproducts and benzene. A number of combinations of columns and separators can be used to recover the EB product and to produce recycle streams of benzene and PEBs for transalkylation. Typically, a first column separates benzene from the remaining heavier components of the transalkylation effluent stream. One or more additional separation columns separate the EB from byproduct streams that contain heavier byproducts, such as DEB and TEB. Heavies byproducts that are not suitable or are not desirable for transalkylation are usually rejected from the process.

Turning now to the dehydrogenation zone, the dehydrogenation produces styrene by dehydrogenating EB formed in the alkylation zone or the transalkylation zone. The dehydrogenation zone, which typically includes a dehydrogenation reactor and its associated separation section, can be of many different variations. The dehydrogenation zone may be any suitable zone and the description that follows is not intended to limit the broad scope of the embodiments of this invention as set forth in the claims.

The dehydrogenation reaction of EB to styrene is highly endothermic. Therefore, passing the reactants through a dehydrogenation catalyst bed results in a decrease in the reactant temperature. The endothermicity of the reaction is such that the temperature decrease removes the reactants from the desired temperature range. The reactants are actually cooled to such an extent that the desired reaction does not progress any further at a commercially feasible rate. The desired or commercially necessary per pass conversion therefore cannot be achieved by simply passing the reactants into contact with a single bed of dehydrogenation catalyst. For this reason, it has become standard commercial practice to in some manner perform interstage reheating. Interstage reheating can be performed by direct heat exchange, by indirect heat exchange, and by the oxidative reheat method. These methods of interstage reheating are described in U.S. Pat. No. 5,043,500, the teachings of which are incorporated herein by reference. Indirect heat exchange using steam is most common, but the arrangement of the dehydrogenation reactor is not critical to the success of the process disclosed herein.

The effluent stream removed from the dehydrogenation reactor is normally heat exchanged to lower its temperature and to recover heat. The effluent stream may be heat exchanged against a stream of steam, a reactant stream of this or another process, or used as a heat source for fractionation, etc. Commercially, the effluent stream is often passed through several heat exchangers, thereby heating a number of different streams. The use of a partial quench to accomplish condensation may be used. Essentially all of the styrene or other product hydrocarbon, most water, and other readily condensable compounds present in the effluent stream are thereby converted to liquids. This produces a mixed phase stream which is passed into a phase separation vessel, where a separation by decantation of the hydrocarbons from the water and non-condensables occurs. The styrene present in the dehydrogenation reactor effluent stream becomes part of a hydrocarbon stream which is withdrawn from the separation vessel and transferred to the dehydrogenation separation section.

The styrene or other product hydrocarbon is recovered from the hydrocarbon stream using any suitable fractionation system. Several suitable fractionation systems are known in the art. This fractionation will preferably yield a relatively pure stream of EB, which is recycled, and an additional stream comprising benzene. Benzene is present in the dehydrogenation effluent usually as a byproduct of dehydrogenation, as is toluene. However, benzene or toluene may also be introduced to the dehydrogenation reactor, as described in U.S. Pat. Nos. 3,409,689 and 3,525,776, or into the dehydrogenation separation section. Styrene is recovered as a third stream, which is withdrawn from the process.

In an embodiment of the process disclosed herein, the benzene-toluene-containing overhead stream of the benzene-toluene recovery column, or of the EB recovery column, in the dehydrogenation section distillation train passes to a benzene-toluene splitter column to produce an overhead stream which is substantially free of toluene. At least a portion of this overhead stream is recycled to the transalkylation reactor. In one embodiment at least 33%, in another embodiment at least 50%, in a third embodiment at least 75%, and in yet another embodiment all of the benzene recovered from the dehydrogenation section distillation train passes to the transalkylation reactor. In one embodiment the benzene recovered from the dehydrogenation section distillation train passes to the transalkylation reactor without undergoing another separation. For example, the benzene passes to the transalkylation reactor without being passed to the separation section(s) for the alkylation reactor effluent or the transalkylation reactor effluent.

As previously mentioned, some of the nitrogen that is introduced as an inhibitor component to the dehydrogenation separation section exits the dehydrogenation separation section in the benzene-containing overhead stream of the benzene-toluene splitter column. The concentration of nitrogen, on an elemental basis, in the benzene-containing overhead stream of the benzene-toluene splitter column is generally from about 0.2 to about 50 wt-ppm, and more commonly from about 0.2 to about 10 wt-ppm, as determined by ASTM D4629-02, Standard Test Method for Trace Nitrogen in Liquid Petroleum Hydrocarbons by Syringe/Inlet Oxidative Combustion and Chemiluminescence Detection, or by ASTM D6069-01, Standard Test Method for Trace Nitrogen in Aromatic Hydrocarbons by Oxidative Combustion and Reduced Pressure Chemiluminescence Detection. These test methods are available from ASTM International, 100 Barr Harbor Drive, P.O. Box 0700, West Conshohocken, Pa., USA. The nitrogen-containing compound present in the overhead stream of the benzene-toluene splitter column may be the same as or different from the inhibitor that was introduced to the process, depending on whether the inhibitor underwent a chemical or physical conversion in the dehydrogenation separation section. The concentration of nitrogen, on an elemental basis, in the overhead stream of the benzene-toluene splitter column depends on many factors such as the boiling range of the inhibitor, the boiling range of the stream, and whether the inhibitor has undergone any conversions.

Since the overhead stream of the benzene-toluene splitter column can be recycled to the transalkylation section and since this overhead stream can contain nitrogen from the inhibitor, in one embodiment at least 33%, in another embodiment at least 50%, in a third embodiment at least 75%, and in yet another embodiment all of the nitrogen recovered from the dehydrogenation section distillation train passes to the transalkylation reactor. In one embodiment the stream carrying this nitrogen from the dehydrogenation section distillation train passes to the transalkylation reactor without undergoing another separation. In particular, the stream passes to the transalkylation reactor without being passed to the separation section(s) for the alkylation reactor effluent or the transalkylation reactor effluent.

A major application of the process disclosed herein is in a styrene process that uses a nitrogen-containing inhibitor, including any of the inhibitors mentioned or referred to herein in the Background of the Invention. The process disclosed herein is also applicable when a sulfur-containing inhibitor is used. It is known that sulfur-containing inhibitors can be added by introducing elemental sulfur to the dehydrogenation separation section or by returning a portion of the heavies (tar) separated from the bottom stream of the styrene column, as described in U.S. Pat. Nos. 3,476,656; 3,408,263; and 3,398,063. Depending on the relative sulfur sensitivities of the alkylation and transalkylation catalysts, it may be desirable to route more of the benzene and/or sulfur-containing inhibitor to the transalkylation reactor instead of to the alkylation reactor. If the detrimental effect of sulfur on the transalkylation catalyst is not as great as that for nitrogen, then sulfur concentrations may be the same or higher than the previously mentioned nitrogen concentrations or the transalkylation catalyst run length may be longer. A person of ordinary skill in the art of hydrocarbon processing can determine these higher concentration limits and arrive at a suitable run length for the transalkylation catalyst without undue experimentation. In the case of sulfur, the recycle stream would be analyzed by ASTM D4045-99, Standard Test Method for Sulfur in Petroleum Products by Hydrogenolysis and Rateometric Colorimetry.

In one embodiment at least 33%, in another embodiment at least 50%, in a third embodiment at least 75%, and in yet another embodiment all of the sulfur recovered from the dehydrogenation section distillation train passes to the transalkylation reactor. In one embodiment the stream carrying this sulfur from the dehydrogenation section distillation train passes to the transalkylation reactor without undergoing another separation. In particular, the stream passes to the transalkylation reactor without being passed to the separation section(s) for the alkylation reactor effluent or the transalkylation reactor effluent.

The FIGURE illustrates an embodiment of the process disclosed herein. For clarity and simplicity, some items associated with the operation of the process have not been shown. These items include flow and pressure control valves, pumps, heat exchangers, temperature and pressure monitoring systems, reactor and fractionated internals, etc., which may be of customary design such representation of this embodiment is not intended to limit the scope of the present invention as set forth in the claims. As used in this description, the term "nitrogen-containing inhibitor" refers to the compound that is introduced to the process via line 66 in the FIGURE. The term "nitrogen-containing component" refers to either the "nitrogen-containing inhibitor" itself or to any nitrogen-containing compound formed from the "nitrogen-containing inhibitor" as a result of any reactions or conversions that take place in the dehydrogenation separation section. Such reactions or conversions can include inhibition of corrosion and/or polymerization.

A stream comprising ethylene enters the process in line 10 and splits into six portions. Each portion flows through one of six lines, 12, 16, 20, 24, 28, and 30, to an upflow alkylation reactor 32. Alkylation reactor 32 contains six beds of alkylation catalyst, including first bed 11 and last bed 13. Lines 10, 14, 18, 22, and 26 deliver ethylene to the six lines, so that each ethylene portion enters the reactor 32 upstream of a bed. For example, ethylene in line 12 enters upstream of bed 11 and ethylene in line 30 enters upstream of bed 13. The other portions enter reactor 32 between beds. Benzene enters reactor 32 through line 49, mixes with the ethylene from line 12, and enters bed 11, where ethylene alkylates benzene. The effluent of each bed except for bed 13 mixes with entering ethylene and flows upward into the next bed. The effluent from bed 13 exits reactor 32 through line 34 and enters benzene distillation column 44.

Besides alkylation effluent in line 34, fresh benzene in line 42 and transalkylation effluent in line 40 enter benzene distillation column 44. The overhead stream of benzene column 44 contains benzene and flows through line 46. Some of this benzene flows through line 45, combines with the stream (if any) flowing in line 100, and flows alone or combined in the stream flowing through line 49 to reactor 32, as described previously. The rest flows through line 47 and combines with a mixture of benzene and PEBs and a nitrogen-containing component flowing in line 59 to form the feed in line 36 to transalkylation reactor 38. The transalkylation reactor 38 contains a single bed 37 of transalkylation catalyst, where benzene and PEBs transalkylate. The bottom stream of benzene column 44 contains EB and PEBs and flows through line 48 to EB distillation column 50. The bottom of EB column 50 contains PEBs and heavier hydrocarbons (heavies) and flows through line 54 to PEB distillation column 56. The overhead stream of PEB column 56 contains PEBs and flows through line 58. This overhead stream combines with a stream containing benzene and a nitrogen-containing component flowing in line 94 to form the mixture flowing in line 59. The bottom stream of PEB column 56, which is sometimes referred to as "flux oil", contains the heavies and is rejected from the process though line 60.

The overhead stream of EB column 50 contains EB and flows through line 52. This overhead stream combines with a stream containing EB flowing in line 82 to form the feed in line 62 to dehydrogenation reactor 64, where EB dehydrogenates to styrene. The dehydrogenation reactor effluent flows in line 65, and a nitrogen-containing inhibitor is injected into the process through line 66. A mixture of dehydrogenation effluent and the nitrogen-containing inhibitor flows through line 67 to effluent splitter distillation column 68. The bottom stream of effluent splitter column 68 contains styrene and heavier compounds such as heavy dehydrogenation byproducts, polymers, and corrosion byproducts. This bottom stream flows through line 72 to styrene distillation column 74. The bottom stream of styrene column 74, which is sometimes referred to as "tar," contains heavy dehydrogenation byproducts, polymers, and corrosion byproducts, and is rejected from the process though line 76. The overhead stream of styrene column 74 containing the valuable styrene product is recovered from the process via line 78.

The overhead stream of effluent splitter column 68 contains EB, and lighter compounds including benzene and toluene, and a nitrogen-containing component and flows through line 70. This overhead stream enters EB recovery distillation column 80. The bottom stream of EB recovery column 80 contains EB and flows through line 82. As previously mentioned, this stream combines with the stream flowing in line 52 to form the dehydrogenation reactor feed in line 62. The overhead stream of EB recovery column 80 contains benzene, toluene, and a nitrogen-containing component and flows through line 84 to benzene-toluene splitter distillation column 86. The bottom stream from benzene-toluene splitter column 86 contains toluene and is rejected from the process through line 88. The overhead stream from benzene-toluene splitter column 86 contains benzene and a nitrogen-containing component and flows through line 90.

Some or all of the overhead stream flowing in line 90 passes to transalkylation reactor 38 by flowing through line 91, flow-regulating valve 92, and line 94. The stream flowing in line 94 combines with the stream flowing in line 58 to form the stream flowing in line 59. As described previously, the stream in line 59 combines with the stream flowing in line 47 to form the transalkylation reactor 38 feed in line 36. The remainder (if any) of the stream flowing in line 90 flows through line 96, flow-regulating valve 98, and line 100. As described previously, the stream (if any) in line 100 combines with the stream flowing in line 45 to form the alkylation reactor 32 feed in line 49.

Regulating valves 92 and 98 can be used to set the desired rate of flow of the stream from line 90 to transalkylation reactor 38. When valves 92 and 98 are both open, one portion of the stream from line 90 flows in the direction of transalkylation reactor 38 and another portion flows the direction of alkylation reactor 32. When valve 92 is open completely and valve 98 is closed completely, the entire stream from line 90 flows in the direction of transalkylation reactor 38. As more of the stream from line 90 flows to transalkylation reactor 38 and less flows to alkylation reactor 32, the alkylation catalyst run length can be extended.

I claim:

1. A process for producing styrene comprising:
   a) reacting benzene and a polyethylbenzene in a transalkylation reactor to form ethylbenzene;
   b) dehydrogenating ethylbenzene in a dehydrogenation reactor to form styrene;
   c) withdrawing a dehydrogenation reactor effluent comprising styrene from the dehydrogenation reactor, and passing at least a portion of the dehydrogenation reactor effluent to a dehydrogenation separation section;
   d) recovering styrene from the dehydrogenation separation section;
   e) introducing a first inhibitor element component to the dehydrogenation separation section;
   f) recovering from the dehydrogenation separation section a recycle stream comprising a second inhibitor element component; and
   g) passing at least 33% of the second inhibitor element component recovered in f) to the transalkylation reactor.

2. The process of claim 1 wherein the first inhibitor element component is the second inhibitor element component.

3. The process of claim 1 wherein at least 50% of the second inhibitor element component recovered in f) passes to the transalkylation zone.

4. The process of claim 1 wherein at least 75% of the second inhibitor element component recovered in f) passes to the transalkylation zone.

5. The process of claim 1 wherein all of the second inhibitor element component recovered in f) passes to the transalkylation zone.

6. The process of claim 1 wherein at least one of the first inhibitor element component and the second inhibitor element component is nitrogen.

7. The process of claim 1 wherein at least one of the first inhibitor element component and the second inhibitor element component is sulfur.

8. The process of claim 1 wherein the transalkylation reactor contains a catalyst comprising a zeolite, and the zeolite is selected from the group consisting of zeolite Y, zeolite beta, ZSM-5, PSH-3, MCM-22, MCM-36, MCM-49, and MCM-56.

9. A process for producing styrene comprising:
   a) passing ethylene and a first portion of a first recycle stream comprising benzene to an alkylation reactor containing an alkylation catalyst to alkylate benzene with ethylene and form ethylbenzene and a polyethylbenzene, and withdrawing from the alkylation reactor an alkylation effluent stream comprising benzene, ethylbenzene, and the polyethylbenzene;
   b) passing at least a portion of the alkylation effluent stream to an alkylation/transalkylation separation section, and withdrawing from the alkylation/transalkylation separation section the first recycle stream comprising benzene, an ethylbenzene stream comprising ethylbenzene, and a polyethylbenzene stream comprising the polyethylbenzene;
   c) passing a second portion of the first recycle stream and at least a portion of the polyethylbenzene stream to a transalkylation reactor containing a transalkylation catalyst to transalkylate benzene with the polyethylbenzene and form ethylbenzene, and withdrawing from the transalkylation reactor a transalkylation effluent stream comprising benzene and ethylbenzene;
   d) passing at least a portion of the transalkylation effluent stream to the alkylation/transalkylation separation section;
   e) passing at least a portion of the ethylbenzene stream to a dehydrogenation reactor to dehydrogenate ethylbenzene and form styrene, and withdrawing from the dehydrogenation reactor a dehydrogenation effluent stream comprising styrene and benzene;
   f) passing at least a portion of the dehydrogenation effluent stream to a dehydrogenation separation section, introducing a first inhibitor component element to the dehydrogenation separation section and withdrawing from the dehydrogenation separation section a second recycle stream comprising benzene;
   g) passing at least 33% of the second recycle stream to the transalkylation reactor; and
   h) recovering styrene from the dehydrogenation separation section and/or second inhibitor component element.

10. The process of claim 9 further characterized in that the passing of at least 33% of the second recycle stream to the transalkylation reactor comprises passing a first portion of the second recycle stream to the transalkylation reactor, a second portion of the second recycle stream passes to the alkylation/transalkylation separation section, and the first portion of the second recycle stream is greater than the second portion of the second recycle stream.

11. The process of claim 9 wherein at least one of the first inhibitor component element and the second inhibitor component element comprises nitrogen.

12. The process of claim 9 wherein the first inhibitor component is the second inhibitor component.

13. The process of claim 9 further characterized in that the transalkylation zone comprises a transalkylation reactor operating at transalkylation conditions comprising a molar ratio of phenyl groups to ethyl group of from about 7:1 to about 2:1 and a liquid hourly space velocity of from about 0.5 to about 5.0 hr$^{-1}$.

14. The process of claim 9 further characterized in that benzene is formed as a byproduct of the dehydrogenating and the benzene recovered from the dehydrogenation reactor comprises benzene formed as a byproduct of the dehydrogenating.

15. The process of claim 9 further characterized in that benzene is passed to the dehydrogenation reactor.

16. The process of claim 9 further characterized in that the at least 33% of the second recycle stream passed to the transalkylation reactor passes to the transalkylation reactor without passing to the alkylation/transalkylation separation section.

17. The process of claim 9 wherein the transalkylation catalyst comprises a zeolite selected from the group consisting of zeolite Y, zeolite beta, ZSM-5, PSH-3, MCM-22, MCM-36, MCM-49, and MCM-56.

* * * * *

UNITED STATES PATENT AND TRADEMARK OFFICE
CERTIFICATE OF CORRECTION

PATENT NO. : 7,276,636 B2 Page 1 of 1
APPLICATION NO. : 11/205657
DATED : October 2, 2007
INVENTOR(S) : John J. Jeanneret It is certified that error appears in the above-identified patent and that said Letters Patent is hereby corrected as shown below:

Column 16: (Claim 9)
Line 27 of "f)": after "recycle stream comprising benzene" insert --and/or second inhibitor component element--
Lines 31-32 of "h)": remove "and/or second inhibitor component element"

Signed and Sealed this

Twelfth Day of August, 2008

JON W. DUDAS
*Director of the United States Patent and Trademark Office*